United States Patent [19]

Bartolone et al.

[11] Patent Number: 5,690,944

[45] Date of Patent: Nov. 25, 1997

[54] COSMETIC COMPOSITIONS CONTAINING LACTATE DEHYDROGENASE INHIBITORS

[75] Inventors: John Brian Bartolone, Bridgeport, Conn.; Christine Marie Penska, Westwood, N.J.; Uma Santhanam, Tenafly, N.J.; Brian David Lang, North Bergen, N.J.

[73] Assignee: Chesebrough-Pond's USA Co., Division of Conopco, Inc., Greenwich, Conn.

[21] Appl. No.: 359,975

[22] Filed: Dec. 20, 1994

[51] Int. Cl.$^6$ .................................................. A61K 6/00
[52] U.S. Cl. ........................................ 424/401; 514/784
[58] Field of Search .......................... 424/401; 514/844, 514/847, 859, 784

[56] References Cited

U.S. PATENT DOCUMENTS

| | | | |
|---|---|---|---|
| 3,823,232 | 7/1974 | Galerne | 424/72 |
| 4,018,927 | 4/1977 | Voorhees | 424/260 |
| 4,242,446 | 12/1980 | Madappally et al. | 435/15 |
| 4,294,852 | 10/1981 | Wildnauer | 514/557 |
| 4,322,496 | 3/1982 | Esders | 435/25 |
| 4,424,234 | 1/1984 | Alderson et al. | 514/558 |
| 4,468,519 | 8/1984 | Krapcho | 548/409 |
| 4,788,196 | 11/1988 | Cross et al. | 514/252 |
| 4,886,801 | 12/1989 | Grozinger et al. | 514/247 |
| 4,906,488 | 3/1990 | Pera | 426/573 |
| 4,950,688 | 8/1990 | Bowser et al. | 514/560 |
| 4,985,547 | 1/1991 | Yano et al. | 536/41 |
| 5,028,416 | 7/1991 | Yano et al. | 424/59 |
| 5,071,971 | 12/1991 | Yano et al. | 536/4.1 |
| 5,091,171 | 2/1992 | Yu et al. | 424/642 |
| 5,175,321 | 12/1992 | Ohashi et al. | 554/63 |
| 5,250,290 | 10/1993 | Giacomoni et al. | 424/59 |
| 5,451,405 | 9/1995 | Zhang et al. | 424/401 |
| 5,545,402 | 8/1996 | Watkinson | 424/94.63 |
| 5,547,989 | 8/1996 | Chamness | 514/558 |
| 5,561,107 | 10/1996 | Jaynes et al. | 514/12 |
| 5,561,158 | 10/1996 | Yu et al. | 514/557 |

FOREIGN PATENT DOCUMENTS

| | | |
|---|---|---|
| 140589 | 5/1985 | European Pat. Off. . |
| 413 528 A1 | 2/1991 | European Pat. Off. . |
| 484 199 A1 | 5/1992 | European Pat. Off. . |
| 565 785 A1 | 10/1993 | European Pat. Off. . |
| 60-058150 | 4/1985 | Japan . |
| 596239 | 2/1978 | U.S.S.R. . |
| WO 91/07982 | 6/1991 | WIPO . |
| WO 91/07982 | 12/1995 | WIPO . |

OTHER PUBLICATIONS

Braibanti et al., "Protonation Constant of Oxamic Acid in Aqueous Solution and in Water–Tetrahydrofuran Mixture, at Different Temperatures and Ionic Strengths", Inorg. Chim. Acta, vol. 4, No. 4, issued 1970, pp. 529–532.

Vermeulen et al., "N–Substituted Oxamates as Inhibitors of Lactate Dehydrogenase", S. Afr. J. Sci., vol. 77, No. 12, issued Dec. 1981, pp. 566–568.

Rohde et al., "Contact Lens–Induced Edema In–Vitro Amelioration by Lactate Dehydrogenase Inhibitors", Curr Eye Res, vol. 5, No. 10, issued Oct. 1986, pp. 751–758.

Wang, Jean Fu, "Kinetic and Mechanistic Studies: I. Direct Determination of Self–Exchange–Transfer Rate Constants of Nickel (III,II) Complexes by Nickel–61 EPR Line Broadening. II. Kinetics of the Hydrolysis of 1–Cyanoformamide, Oxamide, and Oxamic Acid in Hydrochloric Acid Solutions", Diss. Abstr. Int. B, vol. 50, No. 3, issued 1989, p. 931, Full Dissertation Available From University Microfilms Int., Order No. DA8912015, pp. 1–146.

Abstract of Patent Application No. JP6157284.

Linnane, Anthony W., et al., "Mitochondrial DNA Mutation and the Ageing Process: Bioenergy and Pharmacological Intervention", Mutation Research, vol. 275, (1992) pp. 195–208.

Nishitani, Koji et al., "Lactate Dehydrogenase Isozyme Patterns of Normal Human Fibroblasts and their In Vitro–transformed Counterparts Obtained by Treatment with Co–60 Gamma–Rays, SV40 or 4–Nitroquinoline 1–oxide", Gann, 72, Apr. 1981, pp. 300–304.

Fleischmajer, Raul, M.D., et al., "Lactate Dehydrogenase Isozyme Patterns in Blister Fluids", The Journal of Investigative Dermatology, vol. 50, No. 5 (1968), pp. 405–408.

Godfredson et al., "1,6–dihydro–NAD as an Humidity Induced lactate dehydrogenase inhibitor in NADH Preparations", Carlsberg. Res. Comm., 43 (3), (1978), pp. 171–175.

Sheffield et al., "Synthesis of Some 4 Pyridyl Pyruvic Acids as Potential Inhibitors", J. Chem. Soc. Perkin Trans. I, No. 20, 1972, pp. 2506–2512.

Meany et al., "N–substituted Oxamates as Inhibitors of Lactate Dehydrogenase", S. Afr. J. Sci, vol. 77, No. 12, (1981), pp. 566–568.

Nisselbaum et al., "Comparison of the Actions of Human Brain, Liver and Heart Lactic Dehydrogenase Variants on Nucleotide Analogues", J. Biol. Chem., 220, 9, (1964).

Warren, "Catalysis of Both Oxidation and Reduction of Glycoxylate by Pig Heart Lactate Dehydrogenase", J. Biol. Chem. 245, 7, (1970).

Co–pending application Serial No. 08/359,759.

Primary Examiner—Melvyn I. Marquis
Assistant Examiner—Robert H. Harrison
Attorney, Agent, or Firm—Rimma Mitelman

[57] ABSTRACT

Inhibitors of lactate dehydrogenase stimulate keratinocyte proliferation and collagen synthesis in cutaneous tissues. The inhibitors are used preferably with certain co-active ingredients such as pyruvic acid, acetic acid, acetoacetic acid, β-hydroxybutyric acid, a Krebs cycle pathway metabolite, an aliphatic saturated or an unsaturated fatty acid containing from 8 to 26 carbon atoms, an ω-hydroxy acid containing from 22 to 34 carbon atoms, glutamic acid, glutamine, valine, alanine, leucine, and mixtures thereof.

8 Claims, No Drawings

COSMETIC COMPOSITIONS CONTAINING LACTATE DEHYDROGENASE INHIBITORS

FIELD OF THE INVENTION

The invention relates to compositions for topical application to human skin, hair, or nails, which compositions contain an inhibitor of lactate dehydrogenase and to methods of using the compositions for treatment and conditioning of skin, hair, or nails.

BACKGROUND OF THE INVENTION

In recent years cosmetic compositions which improve the appearance of skin have become popular with consumers. There is at the present time a demand for cosmetic compositions which counteract or prevent the visible signs of aged and/or dry skin.

Skin cell proliferation is a process required for growth and repair, and it decreases with aging or photodamage. The synthesis of collagen (a predominant skin protein) also decreases with aging or photodamage. The present invention is based at least in part on the discovery that increased skin cell proliferation and collagen synthesis, which, in turn, is associated with improved condition and appearance of the skin, can be attained by incorporating a lactate dehydrogenase inhibitor into topical treatment compositions.

Cutaneous tissues (skin cells, hair follicles, nails) obtain glucose, (the source of bioenergy) predominantly from blood. Glucose is then enzymatically degraded to pyruvate. Pyruvate is subsequently metabolized within the cutaneous tissues via at least three routes. In the first route, pyruvate is oxidized to form the acetyl group of acetyl-coenzyme A, which is then oxidized completely to $CO_2$ and $H_2O$ via the Krebs cycle. In the second route, pyruvate is reduced to lactate. In the third route, pyruvate serves as a precursor for biosynthesis of three amino acids (valine, alanine, and leucine).

The second route is inefficient in terms of energy production. Specifically, conversion of one glucose molecule to lactate yields only about 5–7% of the total energy that can be set free if the glucose is oxidized completely via Krebs cycle to $CO_2$ and $H_2O$.

Although it is known that pyruvate is metabolized in cutaneous tissue via at least three routes and that the conversion of pyruvate to lactate appears to be a predominant route, it is not known exactly what fraction of pyruvate is metabolized via each of the three routes. The relationship between aging and energy generation in cutaneous tissues is not entirely understood, although it has been suggested that cellular bioenergy loss accompanies aging. See e.g., Linnane, Anthony W., et al. "Mitochondrial DNA Mutation and the Ageing Process: Bioenergy and Pharmacological Intervention", *Mutation Research*, Vol. 275 (1992) pp. 195–208.

Accordingly, it is an object of the present invention to provide compositions for treatment of skin, hair, or nails.

It is another object of the present invention to provide a skin treatment composition containing an inhibitor of lactate dehydrogenase.

It is another object of the invention to provide a method for treating or preventing the appearance of wrinkled, flaky, aged, photodamaged skin or skin disorders.

These and other objects of the invention will become more apparent from the detailed description and examples which follow.

SUMMARY OF THE INVENTION

The above objects are attained by the present invention which includes, in part, a novel composition for topical application to human skin, hair or nails, the composition comprising:

(i) from about 0.001% to about 20% of an inhibitor of lactate dehydrogenase; selected from the group consisting of oxamic acid, an N-substituted oxamic acid, β-chlorolactic acid, thiolactic acid, 1,6-dihydro NAD, 4-pyridyl pyruvic acid, quinoline-2-carboxylic acid, suramin sodium, isoquinoline, papaverine, berberine, and mixtures thereof; and (ii) cosmetically acceptable vehicle for the lactate dehydrogenase inhibitor.

In the preferred embodiment of the invention, in order to maximize the efficacy of the inventive compositions, a co-active ingredient is included which is selected from the group consisting of pyruvic acid, acetic acid, acetoacetic acid, β-hydroxybutyric acid, a Krebs cycle pathway metabolite, an aliphatic saturated or an unsaturated fatty acid containing from 8 to 28 carbon atoms, an ω-hydroxy acid containing from 22 to 34 carbon atoms, glutamic acid, glutamine, valine, alanine, leucine, and mixtures thereof. Most preferably, the co-active ingredient is selected from the group consisting of Krebs cycle metabolites, i.e., citric acid, isocitric acid, cis-aconitic acid, 2-ketoglutaric acid, succinic acid, fumaric acid, malic acid, oxaloacetic acid, and mixtures thereof. D, DL or L-stereoisomeric forms of citric, isocitric and malic acid may be present. L-stereoform is most preferred in order to maximize the efficacy of the inventive compositions.

The present invention also includes a method of treating and improving the condition of skin, hair and nails which method includes applying to the skin, hair, or nails a composition containing the lactate dehydrogenase inhibitor described above in a cosmetically acceptable vehicle.

A particularly preferred use of the inventive compositions is for improving or preventing the appearance of wrinkled, flaky, aged, photodamaged skin, the appearance of age spots, and treating skin disorders. The compositions according to the invention are intended for topical application to mammalian skin which is already in dry, flaky, wrinkled, aged, photodamaged condition or which suffers from a skin disorder, or, in the alternative, the inventive compositions may be applied prophylactically to normal healthy skin to prevent or reduce the deteriorative changes.

DETAILED DESCRIPTION OF THE INVENTION

Lactate Dehydrogenase Inhibitor

An inhibitor of lactate dehydrogenase is the essential ingredient of the inventive compositions.

Lactate dehydrogenase appears in animal tissues as five different isozymes. All the lactate dehydrogenase isozymes contain four polypeptide chains, each of molecular weight about 33,500, but the five isozymes contain varying ratios of two kinds of polypeptide chains which differ in composition and sequence. The A chains (also designated M for muscle) and the B chains (also designated H for heart) are coded by two different genes. In skeletal muscle the lactate dehydrogenase isozyme contains four A chains. In heart the predominant isozyme contains four B chains. The lactate dehydrogenase isozymes in other tissues are a mixture of five possible forms which may be designated A4, A3B, A2B2, AB3 and B4. The different lactate dehydrogenase isozymes differ significantly. For instance, the properties of LDH isozyme A4 favor rapid reduction of pyruvate to lactate in skeletal muscle, whereas the properties of isozyme B4 tend to favor rapid oxidation of lactate to pyruvate in the heart. Some evidence exists that the predominant isozyme found in skin is A4, although other isozymes are present at least to some extent. See Nishitani, Koji et al., "Lactate Dehydrogenase Isozyme Patterns of Normal Human Fibroblasts and their In Vitro-transformed Counterparts Obtained by Treatment with Co-60 Gamma-Rays, SV40 or 4-Nitroquinoline 1-oxide", Gann, 72, April 1981, pp. 300–304; Fleischmajer, Raul, M. D., et al., "Lactate Dehydrogenase Isozyme Patterns in Blister Fluids", *The Journal of Investigative Dermatology*, Vol, 50, No. 5 (1968), pp. 405–408. It is expected, however, that a lactate dehydrogenase inhibitor will inhibit all isozymes of lactate dehydrogenase, at least to some degree.

Suitable lactate dehydrogenase inhibitors are as follows: oxamic acid, an N-substituted oxamic acid, β-chlorolactic acid, thiolactic acid, 1,6-dihydro NAD, 4-pyridyl pyruvic acid, quinoline-2-carboxylic acid, suramin sodium, isoquinoline, papaverine, berberine, and mixtures thereof. Examples of N-substituted oxamic acid include N-alkyl substituted of oxamic acid N-aryl substituted oxamic acid and N,N-alkylaryl substituted oxamic acid (e.g., ethyl N-N-benzyl-methyl oxamic acid). Oxamic acid, β-chlorolactic acid, thiolactic acid, quinoline-2-carboxylicacid, suramin sodium, isoquinoline, papaverine, berberine are available from Sigma. Suramin sodium is available from Bayer.

1,6-dihydro NAD may be synthesized as described by Godtfredson et al., "1,6-dihydro-NAD as an Humidity Induced lactate dehydrogenase inhibitor in NADH Preparations", Carlsberg. Res. Comm., 43 (3), 171–175 (1978), which is incorporated by reference herein. 4-pyridyl pyruvic acid may be synthesized as described by Sheffield et al., in "Synthesis of Some 4 pyridyl pyruvic acids as potential inhibitors", J. Chem Soc. Perkin Trans. I, No. 20, 1972, pp. 2506–2512, which is incorporated by reference herein. N-substituted oxamic acid may be synthesized as described by Meany et al. in "N-substituted Oxamates as Inhibitors of Lactate Dehydrogenase", S. Afr. J. Sci, vol. 77, No. 12, pp. 566–568, 1981, which is incorporated by reference herein.

The lactate dehydrogenase inhibitor is present in the inventive compositions in an amount of from about 0.001% to about 20% by weight of the composition. Preferably, in order to maximize efficacy and to minimize cost, the amount is from about 1% to about 10%, most preferably from about 4% to about 8%.

The suitability of a particular inhibitor for treatment of a particular cutaneous tissue may be determined by measuring the activity of lactate dehydrogenase in the presence of the inhibitor, as described in Example 1 herein.

In the preferred embodiment of the invention, the inventive compositions are skin treatment compositions, wherein the lactate dehydrogenase inhibitor is selected from the group consisting of oxamic acid, thiolactic acid, and mixtures thereof, in order to maximize efficacy and stability and to minimize cost. For these reasons, most preferably, the lactate dehydrogenase inhibitor in skin treatment compositions is oxamic acid.

Cosmetically Acceptable Vehicle

The composition according to the invention also comprises a cosmetically acceptable vehicle to act as a dilutant, dispersant or carrier for the active components in the composition, so as to facilitate their distribution when the composition is applied to the skin, hair and/or nails.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

The cosmetically acceptable vehicle will usually form from 5 to 99.9%, preferably from 25 to 80% by weight of the emulsion, and can, in the absence of other cosmetic adjuncts, form the balance of the composition.

Preferred Co-active Ingredient

According to the present invention, the performance of the lactate dehydrogenase inhibitor can be substantially enhanced by the inclusion into the composition of a co-active ingredient selected from the group consisting of pyruvic acid, acetic acid, acetoacetic acid, β-hydroxybutyric acid, a Krebs cycle pathway metabolite, an aliphatic saturated or an unsaturated fatty acid containing from 8 to 26 carbon atoms, an ω-hydroxy acid containing from 22 to 34 carbon atoms, glutamic acid, glutamine, valine, alanine, leucine, and mixtures thereof.

The term "Krebs cycle pathway metabolite" as used herein means citric acid, isocitric acid, cis-aconitic acid, 2-ketoglutaric acid, succinic acid, fumaric acid, malic acid, oxaloacetic acid, and mixtures thereof.

Suitable examples of saturated or unsaturated fatty acid containing from 8 to 26 carbon atoms include, but are not limited to lauric, palmitic and linoleic acids. Suitable examples of ω-hydroxy acid containing from 22 to 34 carbon atoms include but are not limited to 22-hydroxy docosanoic acid; 23-hydroxy tricosanoic acid; 24-hydroxy tetracosanoic acid; 30-hydroxy triacontanoic acid; 31-hydroxy untriacontanoic acid; 32-hydroxy dotriacontanoic acid; 33-hydroxy tritriacontanoic acid.

The preferred co-active ingredient included in the inventive compositions is selected from pyruvic acid, acetic acid, acetoacetic acid, β-hydroxybutyric acid, a Krebs cycle pathway metabolite, and mixtures thereof, and most preferably is selected from Krebs cycle pathway metabolites, particularly 2-ketoglutaric acid, L-malic acid, and mixtures thereof, in order to optimize efficacy and stabilty at a minimum cost.

The preferred co-active ingredient is present in the inventive compositions in an amount of from about 0.01% to about 20% by weight of the composition.

Preferably, in order to maximize efficacy and to minimize cost, the amount is from about 1% to about 10%, most preferably from about 4% to about 8%.

pH of the Composition

The pH of the inventive compositions is important in order to attain the penetration of active ingredients into skin. Generally, the pH of the inventive compositions is in a range of from about 3 to about 8. Preferably, in order to maximize penetration, the pH is in the range of from about 3 to about 5, most preferably pH is in the range of from 3.5 to 4.5.

Several of lactate dehydrogenase inhibitors and the co-active ingredients used herein are acids. It should be noted that in order to function as a lactate dehydrogenase inhibitor some of these acids have to be in a salt form.

However, depending on the pH of the composition and the pKa of a particular acid employed, the salt may be present in the composition in the form of an acid, or in the form of an acid/salt mixture. It should be understood that the relative fractions of salt and acid in the salt/acid mixture in the composition may vary once the composition is applied to skin, depending on the differences between the pH of skin (typically, slightly acidic, around 6–7, but varies from individual to individual and depends on skin condition) and the pH of the composition. It should also be understood that if a compound satisfies a lactate dehydrogenase inhibition test conducted at pH 7.0–7.5 as described in Example 1, the compound is suitable for inclusion in the composition. For instance, if the pH of the composition is about 3–4, a major fraction or all of oxamate salt in the composition is present in the composition in the form of oxamic acid. However, such composition is still within the scope of the present invention because after application to skin, at least some of the acid will be converted into a salt and will be able to function as a lactate dehydrogenase inhibitor. Put another way, if a compound present in the composition satisfies a lactate dehydrogenase inhibition test at pH 7.0–7.5, the composition is within the scope of the invention regardless of the pH of the composition.

For the sake of illustration, the following active and co-active ingredients may be present in the inventive compositions in the form of a salt: oxamic acid, N-substituted oxamic acid, β-chlorolactic acid, thiolactic acid, 4-pyridyl pyruvic acid, quinoline-2-carboxylic acid, pyruvic acid, acetic acid, acetoacetic acid, β-hydroxybutyric acid, an aliphatic saturated or an unsaturated fatty acid containing from 8 to 26 carbon atoms, an ω-hydroxy acid containing from 22 to 34 carbon atoms, glutamic acid, citric acid, isocitric acid, cis-aconitic acid, 2-ketoglutaric acid, succinic acid, fumaric acid, malic acid, oxaloacetic acid.

Suitable salts which may be present in the composition include but are not limited to sodium, potassium, ammonium, triethanolamine, calcium, lithium salts. The salts may be obtained commercially or they may be prepared by methods known in the art, e.g., neutralizing an acid with a suitable base, such as hydroxide bases of ammonium, potassium, sodium.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents, skin anti-wrinkling agents, anti-dandruff agents, hair conditioners and hair growth stimulants.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxy-cinnamate and 2-hydroxy-4-methoxy benzophenone are commercially available under the trademarks, Parsol MCX and Benzophenone-3, respectively.

The exact amount of sunscreen employed in the emulsions can vary depending upon the degree of protection desired from the sun's UV radiation.

A preferred optional active ingredient to be included in the inventive composition are ceramides which play an important role in the production and maintenance of the water permeability barrier of the skin. Suitable ceramides and synthetic analogues thereof are disclosed in European Patent Application No. 534 286, European Patent Application No. 282 816, European Patent Application No. 227 994, U.S. Pat. No. 5,175,321, U.S. Pat. No. 4,985,547, U.S. Pat. No. 5,028,416, U.S. Pat. No. 5,071,971, Japanese Patent Application No. 63192703, U.S. Pat. No. 4,468,519, and U.S. Pat. No. 4,950,688, all U.S. patents are incorporated by reference herein. Caramides or their synthetic analogues may be present in the inventive compositions at a level of from about 0.00001% to about 5%, preferably from about 0.0001% to about 1%, optimally from about 0.01% to 0.5%.

Another preferred optional ingredient is selected from essential fatty acids (EFAs), i.e., those fatty acids which are essential for the plasma membrane formation of all cells. In keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic aid, columbinic acid, eicosa-(n-6,9, 13)-trienoic acid, arachidonic acid, γ-linolenic acid, timnodonic acid, hexaenoic acid and mixtures thereof. A good suitable source of essential fatty acids is sunflower oil or primrose oil.

The inventive compositions may include hydroxyacids. The hydroxy acid can be chosen from α-hydroxy acids, β-hydroxyacids, other hydroxycarboxylic acids (e.g., dihydroxycarboxylic acid, hydroxy-dicarboxylic, hydroxytricarboxylic) and mixtures thereof or combination of their stereoisomers (DL, D or L).

Preferably, the hydroxy acid (ii) is chosen from α-hydroxy acids having the following general structure:

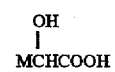

where

M is H— or $CH_3(C_fH_g)_h$—, f is an integer of from 1 to 27, g is an integer of from 2 to 54, and h is 0 or 1.

Even more preferably, the hydroxy acid is chosen from 2-hydroxyoctanoic acid, hydroxylauric lactic acid, and glycolic acid, and mixtures thereof. When stereoisomers exist, L-isomer is most preferred.

The keto acids can be chosen from α-keto acids, β-keto acids and mixtures thereof.

A particularly preferred α-keto acid is 2-keto octanoic acid.

Preferably the amount of the hydroxy acid component (ii) present in the composition according to the invention is from 0.01 to 20%, more preferably from 0.05 to 10%. and most preferably from 0.1 to 3% by weight.

Surfactants, which are also sometimes designated as emulsifiers, may be incorporated into the cosmetic compositions of the present invention. Surfactants can comprise anywhere from about 0.5% to about 30%, preferably from about 1% to about 15% by weight of the total composition.

Surfactants may be cationic, nonionic, anionic, or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neodol" designation. Copolymers of polyoxypropylene-polyoxyethylene, available under the Pluronic trademark sold by the BASF Corporation, are sometimes also useful. Alkyl polyglycosides available from the Henkel Corporation similarly can be utilized for the purposes of this invention.

Anionic-type surfactants may include fatty acid soaps, sodium lauryl sulphate, sodium lauryl ether sulphate, alkyl benzene sulphonate, mono and/or dialkyl phosphates and sodium fatty acyl isethionate.

Amphoteric surfactants include such materials as dialkylamine oxide and various types of betaines (such as cocoamido propyl betaine).

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust bean gum. Under certain circumstances the thickening function may be accomplished by a material also serving as a silicone or emollient. For instance, silicone gums in excess of 10 centistokes and esters such as glycerol stearate have dual functionality.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, imidazolidinyl urea, sodium dehydroxyacetate and benzyl alcohol. Preservatives will usually be employed in amounts ranging from about 0.5% to 2% by weight of the composition.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

Use of the Composition

The composition according to the invention is intended primarily as a product for topical application to human skin, especially as an agent for reducing the permeability to water of the skin, particularly when the skin is dry or damaged, in order to reduce moisture loss and generally to enhance the quality and flexibility of skin. The composition can also be applied to hair and nails.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing cosmetically acceptable composition as herein defined.

The following specific examples further illustrate the invention but the invention is not limited thereto.

EXAMPLE 1

Procedure for Testing Lactate Dehydrogenase (LDH) Inhibition

All reagents were purchased from Sigma Chemical Co., St. Louis, Mo., USA. Sigma procedure No. 500 was modified for our purposes. One mL of pyruvate substrate (Sigma 500L-1, pH=7.5) was added to a vial containing 1 mg NADH (Sigma 340-101). In a 96-well plate, the following components were added to each test well: 10 µl pyruvate/

NADH mixture, and 10 μl cell lysate. For preparation of cell lysates, neonatal human keratinocytes or fibroblasts (Clonetic Corp., San Diego, Calif.) were cultured in tissue culture plates (Corning, USA). Cells were scraped in PBS (pH=7.4) and this solution was used as a source of L-lactate dehydrogenase. If such cell lysate was not available, a commercial preparation of L-lactic dehydrogenase (E.C. 1.1.1.27), Sigma L9889, from porcine heart could be used in place of the cell lysate. For positive control, the inhibitor was replaced with 10 μl of PBS. For blank determination, the lysate or enzyme was replaced with 10 mL of PBS. After mixing, the plate was incubated for 30 minutes at 37° C. Then 20 μl of color reagent (Sigma 505-2) was added to each well. After 20 minutes at room temperature, 150 μl of 0.4N NaOH was added, and the plate was read for absorbance at 490 nm in a Dynatech MR 7000 Microplate Reader.

To calculate % inhibition, the control activity (CA) was first determined by subtracting the absorbance of the positive control from the blank. Then the activity in the presence of the inhibitor (IA) was calculated by subtracting the appropriate absorbance from the blank. % Inhibition was then calculated as: [(CA−IA)/CA]*100%.

TABLE 1

Inhibitors of Keratinocyte Lactate Dehydrogenase (% Inhibition)

| | | CONCENTRATION (mM) | | | |
|---|---|---|---|---|---|
| Code | Inhibitor | 5 | 2.5 | 1.25 | 0.625 |
| A | Oxamate | 97 | 93 | 84 | 71 |
| B | Thio-Lactate | 14 | 8 | 8 | 4 |

TABLE 2

Inhibitors of Fibroblast Lactate Dehydrogenase (% Inhibition)

| | | CONCENTRATION (mM) | | | |
|---|---|---|---|---|---|
| Code | Inhibitor | 5 | 2.5 | 1.25 | 0.625 |
| A | Oxamate | 96 | 92 | 87 | 76 |
| B | Thio-Lactate | 11 | 11 | 8 | 7 |
| C | Glycolate | 0 | 0 | 0 | 0 |
| D | Malonate | 0 | 0 | 0 | 0 |
| E | L-lactate | 0 | 0 | 0 | 0 |
| F | D-lactate | 0 | 0 | 0 | 0 |
| G | Pyrazole | 0 | 0 | 0 | 0 |
| H | Methyl pyrazole | 0 | 0 | 0 | 0 |
| I | Glycinate | 0 | 0 | 0 | 0 |
| K | L-malate | 0 | 0 | 0 | 0 |

The results in Tables 1 and 2 demonstrate an effective procedure for ascertaining whether a compound inhibits lactate dehydrogenase. The results also demonstrate that compounds A and B (Tables 1 and 2) were effective inhibitors of LDH, while compounds C–K (Table 2) did not inhibit LDH.

EXAMPLE 2

Effect of LDH Inhibitors on Keratinocyte Proliferation

Procedure for Measuring Keratinocyte Proliferation

Normal human epidermal keratinocytes (NHEK) derived from neonatal foreskin were used for all experiments. Media were purchased from Clonetics Corp., San Diego, Calif. Cell stocks frozen in passage 2 were grown in Keratinocyte Growth Medium (KGM) and passaged when 70–80% confluent. Cells were seeded in 96 well plates (Corning) at a density of 7500 cells/well in KGM. After 24 hours, cells were rinsed and dosed with test compounds in 200 μl of Keratinocyte Basal Medium (KBM). Plates were incubated for three days at 37° C., 5% $CO_2$. Cell proliferation was estimated by assaying for DNA content by a fluorometric method described by Rago et al. (Analytical Biochemistry, 191:31–34, 1990). Medium was removed and cells were rinsed with phosphate buffered saline solution. 100 μl of sterile distilled water was added to each well and plates were frozen at −70° C. for one and a half hours. Plates were thawed for one hour at which time 100 μl of a 20 ug/ml solution of Bisbenzimide H33258 fluorochrome (Calbiochem Corp., La Jolla, Calif.) was added to each well. The fluorochrome was prepared just prior to use in 10 mM Tris, 1 mM EDTA, 4M NaCl, pH 7.4. Plates were read in a Millipore Cytofluor fluorescent plate reader to quantify DNA (excitation 360 nm, emission 460 nm). Percent increase over control was calculated from blank-corrected readings as (treated−untreated)/(untreated)*100%. Each data point in the Tables below represents a mean of 5 or 6 replicates. The results that were obtained are summarized in Tables 3 and 4.

TABLE 3

Effect of Oxamate on Keratinocyte Proliferation (% Increase Over Control)

| | Concentration (mM) | | | | | | |
|---|---|---|---|---|---|---|---|
| Test | 20 | 10 | 5.0 | 2.5 | 1.25 | 0.025 | 0.313 |
| A | 0 | 20 | 28 | — | — | — | — |
| B | 0 | 33 | 48 | 39 | 28 | — | — |
| C | 0 | 0 | 0 | 0 | — | — | — |
| D | — | 0 | 23 | 32 | 24 | 20 | 18 |
| E | — | 0 | 20 | 25 | 40 | 19 | 32 |

— Concentration not tested

TABLE 4

Effect of Other LDH Inhibitors on Keratinocyte Proliferation (% increase over control)

| | | Concentration (mM) | | | | |
|---|---|---|---|---|---|---|
| Test | Inhibitor | 5 | 2.5 | 1.25 | 0.625 | 0.313 |
| F | Thiolactate | 0 | 5 | 27 | 29 | 9 |

The results in Tables 3 and 4 indicate that LDH inhibitors stimulate keratinocyte proliferation. Test C in Table 3 does not appear to be a representative dose response curve of the effect of oxamate on keratinocyte proliferation because it was the only experiment of the five in which oxamate did not stimulate keratinocyte proliferation at the concentrations tested. It is possible that the dose response has shifted in Test C as a result of the cells having different metabolic requirements as compared to the cells in the other four experiments. Therefore, if lower concentrations had been tested, there most likely would have been an effect. The dose response appears to be a "bell shape curve" response. It should be noted that the response obtained at a particular concentration differs from test to test (see Table 3), as a result of the cells in different experiments having different metabolic requirements. Therefore, various actives should be compared within the same experiments only.

EXAMPLE 3

The procedure of Example 2 was repeated except that various co-active ingredients were tested for their ability to stimulate keratinocyte proliferation.

The results that were obtained are summarized in Tables 5–9.

TABLE 5

Effect of L-Malate on Keratinocyte Proliferation
(% Increase Over Control)

Concentration (mM)

| Test | 20 | 10 | 5.0 | 2.5 | 2.0 | 1.25 | 0.625 | 0.313 | 0.2 | 0.15 | 0.02 | 0.002 |
|---|---|---|---|---|---|---|---|---|---|---|---|---|
| A | ND | 0 | 25 | 49 | ND | 53 | 53 | 43 | ND | 19 | ND | ND |
| B | ND | 26 | 67 | 60 | ND | 78 | 79 | 78 | ND | 89 | ND | ND |
| C | ND | ND | 0 | 0 | ND | 12 | 33 | 28 | ND | 9 | ND | ND |
| D | ND | ND | 20 | 39 | ND | 25 | 36 | 29 | ND | 33 | ND | ND |
| E | ND | 256 | ND | ND | 88 | ND | ND | ND | 36 | ND | 27 | 34 |
| F | 86 | 88 | ND | ND | 21 | ND | ND | ND | 19 | ND | ND | ND |
| G | 11 | 59 | ND | ND | 28 | ND | ND | ND | 29 | ND | ND | ND |

TABLE 6

Effect of Citrate on Keratinocyte Proliferation
(% Increase Over Control)

Concentration (mM)

| Test | 10 | 5.0 | 2.5 | 2.0 | 1.25 | 1.0 | 0.6 | 0.3 | 0.2 | 0.15 | 0.1 | 0.02 | 0.01 | 0.002 |
|---|---|---|---|---|---|---|---|---|---|---|---|---|---|---|
| A | ND | ND | ND | ND | ND | ND | ND | ND | 33 | ND | ND | 40 | ND | 30 |
| B | ND | ND | ND | ND | ND | ND | ND | ND | 7 | ND | ND | 17 | ND | 0 |
| C | ND | ND | ND | ND | ND | 20 | ND | ND | ND | ND | 40 | ND | 25 | ND |
| D | 0 | 0 | 0 | ND | 18 | ND | 35 | 39 | ND | 18 | ND | ND | ND | ND |

TABLE 7

Effect of Acetate on Keratinocyte Proliferation
(% Increase Over Control)

Concentration (mM)

| Test | 20 | 10 | 5.0 | 2.5 | 2.0 | 1.25 | 0.625 | 0.313 | 0.2 | 0.156 | 0.07 | 0.02 | 0.002 |
|---|---|---|---|---|---|---|---|---|---|---|---|---|---|
| A | ND | 63 | | | 46 | | | | 43 | | | 31 | 22 |
| B | 0 | 0 | | | 19 | | | | 12 | | | ND | ND |
| C | | 0 | 0 | 11 | | 2 | 9 | 32 | | 13 | ND | | |
| D | | ND | 18 | 44 | | 42 | 57 | 56 | | 47 | 50 | | |
| E | | ND | ND | ND | | ND | ND | 24 | | 6 | 0 | | |
| F | | 0 | 7 | 33 | | 35 | 34 | 5.0 | | ND | ND | | |
| G | | 0 | 18 | 12 | | 24 | 11 | 38 | | ND | ND | | |

TABLE 8

Effect of Isocitrate on Keratinocyte Proliferation
(% Increase Over Control)

Concentration (mM)

| Test | 10 | 5.0 | 2.5 | 2.0 | 1.25 | 0.625 | 0.313 | 0.2 | 0.156 | 0.02 | 0.002 | 0.0002 |
|---|---|---|---|---|---|---|---|---|---|---|---|---|
| A | 0 | | | 40 | | | | 62 | | 63 | 39 | ND |
| B | ND | | | 30 | | | | 29 | | 30 | 20 | 0 |
| C | 0 | 18 | 32 | | 40 | 32 | 40 | | 32 | | | |

TABLE 9

Effect of Oxaloacetate on Keratinocyte Proliferation
(% Increase Over Control)

| Test | Concentration (mM) | | | | | | | | | | | | |
|---|---|---|---|---|---|---|---|---|---|---|---|---|---|
|  | 20 | 10 | 5.0 | 2.5 | 2.0 | 1.25 | 0.6 | 0.3 | 0.2 | 0.15 | 0.02 | 0.08 | 0.002 |
| A | ND | 110 |  | 53 |  |  |  | 22 |  | 15 |  |  | 11 |
| B | 44 | 70 |  | 16 |  |  |  | 20 |  | 30 |  |  | ND |
| C |  |  | 0 | 35 | 40 |  | 18 | 20 | 18 |  | 13 | ND |  |
| D |  |  | 52 | 52 | 37 |  | 37 | 48 | 63 |  | 76 | 56 |  |

The results in Tables 5–9 indicate that various co-active ingredients within the scope of the invention stimulated keratinocyte proliferation.

EXAMPLE 4

Assay for Collagen Synthesis

Neonatal human dermal fibroblasts were purchased from Clonetics Corp., San Diego, Calif. All materials for cell culture were purchased from Life Technologies, NY. Cells were maintained in DMEM with 10% fetal bovine serum and used in passages 5–10. Confluent 96-well plates containing fibroblasts were treated with test materials (0.2 to 20 mM) in serum-free medium for 48 hours. Media was collected and an immunoassay utilizing a monoclonal antibody specific for procollagen 1 (MAB 1912, Chemicon, Temecula, Calif.) was performed to estimate the amount of secreted pro-collagen in the medium. This was carried out in a BioDot SF apparatus according to the manufacturer's instructions (BioRad Labs, CA) and the blot was developed using a Vectastain Kit (PK6104, Vector Labs, CA) as per the manufacturer's directions. Color intensity was quantitated using an Ultroscan XL densitometer (Pharmacia LKB). Fold increase was calculated as (density of treated)/untreated. The results that were obtained are summarized in Table 10.

TABLE 10

Effect of LDH Inhibitors or Co-active Ingredients on Collagen Synthesis

| Inhibitor | Maximum fold over Control |
|---|---|
| Oxamate | 1.4 |
| Acetate | 2.0 |
| Acetoacetate | 2.2 |
| Ketoglutarate | 2.2 |
| L-Malate | 2.6 |
| Succinate | 2.8 |
| Oxaloacetate | 3.0 |
| Glutamate | 3.6 |

EXAMPLE 5

The procedure of Example 2 was employed to test the effect of combination of an LDH inhibitor and a co-active ingredient on keratinocyte proliferation. The results that were obtained are summarized in Tables 11 and 12.

TABLE 11

% Increase Over Control

| Oxamate (mM) | Pyruvate (mM) | | | | | | |
|---|---|---|---|---|---|---|---|
|  | 0 | 0.156 | 0.313 | 0.625 | 1.25 | 2.5 | 5.0 |
| 0 |  | 2 | 0 | 3 | 0 | 7 | 0 |
| 2.5 | 0 | — | — | — | — | — | — |
| 5.0 | 0 | 10 | 18 | 4 | 15 | 0 | 0 |
| 10 | 0 | 8 | 8 | 11 | 13 | 0 | 0 |
| 15 | 0 | 0 | 0 | 0 | 0 | 0 | 0 |
| 20 | 0 | 0 | 0 | 0 | 0 | 0 | 0 |

— Concentration not tested

The results in Table 11 indicate that even when the individual ingredients did not result in increase in keratinocyte proliferation, at the concentration tested in a particular experiment, the combination of those ingredients resulted in a significant increase over control.

TABLE 12

Malate
% Increase Over Control

| Oxamate (mM) | CONCENTRATION (mM) | | | | | | |
|---|---|---|---|---|---|---|---|
|  | 0 | 0.156 | 0.313 | 0.625 | 1.25 | 2.5 | 5.0 |
| 0 |  | 33 | 29 | 36 | 25 | 39 | 20 |
| 0.313 | 32 | — | — | — | — | — | — |
| 0.625 | 19 | — | — | — | — | — | — |
| 1.25 | 40 | 44 | 29 | 44 | 49 | 37 | 20 |
| 2.5 | 25 | 65 | 36 | 74 | 61 | 54 | 20 |
| 5.0 | 20 | 38 | 38 | 58 | 57 | 51 | 7 |
| 10 | 0 | — | — | — | — | — | — |

— Not tested

The results in Tables 11 and 12 demonstrate that the combination of an LDH inhibitor with a preferred co-active ingredient results in substantial enhancement of keratinocyte proliferation.

EXAMPLE 6

This example illustrates a high internal phase water-in-oil emulsion in accordance with the invention.

|  | % w/w |
|---|---|
| Thiolactate | 1 |
| Acetate | 8 |
| Fully hydrogenated coconut oil | 3.9 |
| Neoceramide having the structure (5) | 0.1 |
| Brij 92* | 5 |

-continued

|  | % w/w |
| --- | --- |
| Bentone 38 | 0.5 |
| Preservative | 0.3 |
| MgSO$_4$7H$_2$O | 0.3 |
| Butylated hydroxy toluene | 0.01 |
| Perfume | qs |
| Water | to 100 |

*Brij 92 is polyoxyethylene (2) oleyl ether

EXAMPLE 7

This example also illustrates a high internal phase water-in-oil emulsion in accordance with the invention in which the formulation of Example 6 is prepared but with the following changes:

(i) liquid paraffin employed instead of the fully hydrogenated coconut oil, and;

(ii) oxamate is used in place of thiolactate.

EXAMPLE 8

This example also illustrates a high internal phase water-in-oil emulsion in accordance with the invention in which the formulation of Example 6 is prepared but with the following changes:

β-chlorolactate is used in place of thiolactate.

EXAMPLE 9

This example illustrates an oil-in-water cream containing an lactate dehydrogenase according to the invention.

|  | % w/w |
| --- | --- |
| Oxamate | 4 |
| Acetate | 4 |
| Mineral oil | 4 |
| Thiolactate | 2 |
| Brij 56* | 4 |
| Alfol 16RD** | 4 |
| Triethanolamine | 0.75 |
| Butane-1,3-diol | 3 |
| Xanthan Gum | 0.3 |
| Preservative | 0.4 |
| Perfume | qs |
| Butylated hydroxy toluene | 0.01 |
| Water | to 100 |

*Brij 56 is cetyl alcohol POE (10)
**Alfol 16RD is cetyl alcohol

EXAMPLES 10 AND 11

The following compositions according to the invention represent lotions which can be used in the treatment of dry skin:

|  | % w/w | |
| --- | --- | --- |
|  | 10 | 11 |
| L-malate | 6.0 | 4.0 |
| Thiolactate | 2.0 | 4.0 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilized Demineralized Wtaer | to 100 | to 100 |

EXAMPLE 12

This example illustrates an alcoholic lotion containing a lactate hydrogenase inhibitor according to the invention which is suitable for application to nails.

|  | % w/w |
| --- | --- |
| Oxamate | 4 |
| Dimethylsulphoxide | 10 |
| Ethanol | 40 |
| Antoxidant | 0.1 |
| Perfume | qs |
| Water | to 100 |

EXAMPLES 13 AND 14

The following compositions according to the invention represent lotions which can be used in the treatment of dry, unmanageable hair.

|  | % w/w | |
| --- | --- | --- |
|  | 13 | 14 |
| Pyruvate | 6 | 8 |
| Oxamate | 2 | 1 |
| Perfume | 0.1 | 0.1 |
| Hydroxyethyl cellullose | 0.4 | 0.4 |
| Absolute ethanol | 25 | 25 |
| p-methyl benzoate | 0.2 | 0.2 |
| Sterilized demineralized water | to 100 | to 100 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A composition for topical application to human skin, the composition comprising:

(i) from about 0.001% to about 20% of an inhibitor of lactate dehydrogenase selected from the group consisting of oxamic acid, an N-substituted oxamic acid, 1,6-dihydro NAD, 4-pyridyl pyruvic acid, quinoline-2-carboxylic acid, suramin sodium, isoquinoline, papaverine, berberine, and mixtures thereof; and (ii) from about 0.01% to about 20% by weight of the composition of a co-active ingredient selected from the group consisting of pyruvic acid, acetic acid, acetoacetic acid, β-hydroxybutyric acid, citric acid, isocitric acid, cis-aconitic acid, 2-ketoglutaric acid, succinic acid, fumaric acid, malic acid, oxaloacetic acid, an aliphatic saturated or an unsaturated fatty acid containing from 8 to 26 carbon atoms, an ω-hydroxy acid containing from 22 to 34 carbon atoms, glutamic acid, glutamine, valine, alanine, leucine, and mixtures thereof, (iii) a cosmetically acceptable vehicle for the lactate dehydrogenase inhibitor, wherein the vehicle comprises water; wherein the pH of the composition is from about 3 to about 8; and wherein the lactate dehydrogenase inhibitor acts within the human skin.

2. The composition of claim 1 wherein the lactate dehydrogenase inhibitor is present in an amount of from about 0.1% to about 10% by weight of the composition.

3. The composition of claim 1 wherein the co-active ingredient is selected from the group consisting of pyruvic acid, acetic acid, acetoacetic acid, β-hydroxybutyric acid, citric acid, isocitric acid, cis-aconitic acid, 2-ketoglutaric acid, succinic acid, fumaric acid, malic acid, oxaloacetic acid, and mixtures thereof.

4. The composition of claim 3 wherein the co-active ingredient is selected from the group consisting of pyruvic acid, acetic acid, 2-ketoglutaric acid, L-malic acid, succinic acid, and mixtures thereof.

5. The composition of claim 1 wherein the lactate dehydrogenase inhibitor is selected from the group consisting of oxamic acid, thiolactic acid, and mixtures thereof.

6. The composition of claim 1 wherein the pH of the composition is from about 3 to about 5.

7. A method of treating human skin which comprises applying topically thereto the composition comprising:
   (i) from about 0.001% to about 20% of an inhibitor of lactate dehydrogenase selected from the group consisting of oxamic acid, an N-substituted oxamic acid, β-chlorolactic acid, thiolactic acid, 1,6-dihydro NAD, 4-pyridyl pyruvic acid, quinoline-2-carboxylic acid, suramin sodium, isoquinoline, papaverine, berberine, and mixtures thereof; and
   (ii) a cosmetically acceptable vehicle for the lactate dehydrogenase inhibitor.

8. A method of improving the appearance of wrinkled, flaky, aged, photodamaged skin, the appearance of age spots which comprises applying topically thereto the composition comprising:
   (i) from about 0.001% to about 20% of an inhibitor of lactate dehydrogenase selected from the group consisting of oxamic acid, an N-substituted oxamic acid, 1,6-dihydro NAD, 4-pyridyl pyruvic acid, quinoline-2-carboxylic acid, suramin sodium, isoquinoline, papaverine, berberine, and mixtures thereof; and
   (ii) a cosmetically acceptable vehicle for the lactate dehydrogenase inhibitor.

* * * * *